US010695360B2

(12) United States Patent
Yoshino et al.

(10) Patent No.: US 10,695,360 B2
(45) Date of Patent: Jun. 30, 2020

(54) ADIPONECTIN SECRETION ENHANCER

(71) Applicants: WASHINGTON UNIVERSITY, Saint Louis, MO (US); Oriental Yeast Co., Ltd., Tokyo (JP)

(72) Inventors: Jun Yoshino, Creve Coeur, MO (US); Hisataka Yasuda, Shiga (JP); Hideo Arai, Tokyo (JP); Tetsuro Enomoto, Tokyo (JP)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 15/898,016

(22) Filed: Feb. 15, 2018

(65) Prior Publication Data

US 2018/0228824 A1 Aug. 16, 2018

(30) Foreign Application Priority Data

Feb. 16, 2017 (JP) ................. 2017-027373

(51) Int. Cl.

| | |
|---|---|
| *A61K 31/706* | (2006.01) |
| *A61P 3/04* | (2006.01) |
| *A61K 9/00* | (2006.01) |
| *A61K 31/185* | (2006.01) |
| *A61K 38/06* | (2006.01) |
| *A61K 31/205* | (2006.01) |
| *A61K 31/197* | (2006.01) |
| *A61K 31/122* | (2006.01) |
| *A61K 31/7012* | (2006.01) |
| *A61K 31/7004* | (2006.01) |
| *A61K 36/81* | (2006.01) |
| *A61K 36/9068* | (2006.01) |
| *A61K 36/185* | (2006.01) |
| *A61K 36/77* | (2006.01) |
| *A61K 36/38* | (2006.01) |
| *A61K 31/198* | (2006.01) |
| *A61K 31/165* | (2006.01) |
| *A61K 31/702* | (2006.01) |
| *A23L 33/13* | (2016.01) |
| *A23K 20/153* | (2016.01) |
| *A61P 3/10* | (2006.01) |
| *A61K 45/06* | (2006.01) |
| *A23L 33/20* | (2016.01) |
| *A61K 8/67* | (2006.01) |

(52) U.S. Cl.
CPC .......... *A61K 31/706* (2013.01); *A23K 20/153* (2016.05); *A23L 33/13* (2016.08); *A23L 33/20* (2016.08); *A61K 9/0056* (2013.01); *A61K 9/0095* (2013.01); *A61K 31/122* (2013.01); *A61K 31/165* (2013.01); *A61K 31/185* (2013.01); *A61K 31/197* (2013.01); *A61K 31/198* (2013.01); *A61K 31/205* (2013.01); *A61K 31/702* (2013.01); *A61K 31/7004* (2013.01); *A61K 31/7012* (2013.01); *A61K 36/185* (2013.01); *A61K 36/38* (2013.01); *A61K 36/77* (2013.01); *A61K 36/81* (2013.01); *A61K 36/9068* (2013.01); *A61K 38/063* (2013.01); *A61K 45/06* (2013.01); *A61P 3/04* (2018.01); *A61P 3/10* (2018.01); *A23V 2002/00* (2013.01); *A61K 8/675* (2013.01)

(58) Field of Classification Search
CPC ............................. A61K 31/706; A61K 8/675
USPC .................................................... 514/89, 279
See application file for complete search history.

(56) References Cited

U.S. PATENT DOCUMENTS 7,737,158 B2   6/2010   Imai et al.

FOREIGN PATENT DOCUMENTS

| JP | 2007-527418 A | 9/2007 |
| WO | 2005/065667 A2 | 7/2005 |
| WO | 2014/146044 A1 | 9/2014 |

OTHER PUBLICATIONS

Gomes, A.P., et al., Declining NAD+ Induces a Pseudohypoxic State Disrupting Nuclear-Mitochondrial Communication during Aging, Cell, 2013, 155, 1624-1638.
Mills, K.F., Long-Term Administration of Nicotinamide Mononucleotide Mitigates Age-Associated Physiological Decline in Mice, Cell Metabolism, 2016, 24, 795-806.
Stromsdorfer, K. L., et al., NAMPT-Mediated NAD+ Biosynthesis in Adipocytes Regulates Adipose Tissue Function and Multi-organ Insulin Sensitivity in Mice Cell Reports, 2016, 16, 1-10.
Qiang, L. et al., Adiponectin Secretion Is Regulated by SIRT1 and the Endoplasmic Reticulum Oxidoreductase Ero1-Lalpha Molecular and Cellular Biology, 2007, 27(13), 4698-4707.
Yoshino, J., et al., Nicotinamide Mononucleotide, a Key NAD+ Intermediate, Treats the Pathophysiology of Diet- and Age-Induced Diabetes in Mice Cell Metabolism, 2011, 14, 528-536.

*Primary Examiner* — Kevin E Weddington
(74) *Attorney, Agent, or Firm* — Saul L. Zackson; Zackson Law LLC (57) ABSTRACT

The present disclosure provides for the administration of β-NMN, which increases the secretion of adiponectin. The present disclosure also provides an adiponectin secretion enhancer comprising β-nicotinamide mononucleotide, a pharmaceutically acceptable salt thereof or a solvate thereof, and a dietary supplement containing the aforementioned secretion enhancer, which can be ingested in order to increase the secretion of adiponectin. Also disclosed are methods of treating insulin resistance-related diseases such as of metabolic syndrome, diabetes, hyperlipidemia, fatty liver disease, hypertension, obesity, and arteriosclerosis.

12 Claims, 7 Drawing Sheets

ADIPONECTIN SECRETION ENHANCER

STATEMENT OF GOVERNMENT SUPPORT

This invention was made with government support under DK020579 awarded by the National Institutes of Health. The government has certain rights in the invention.

CROSS REFERENCE TO FOREIGN APPLICATION

This application claims the benefit of and priority to Japanese Patent Application No. 2017-027373 filed on Feb. 16, 2017 under 35 USC § 119. This application is hereby incorporated by reference in its entirety.

TECHNICAL FIELD

The present disclosure relates to a material capable of enhancing secretion of adiponectin from adipocytes, and an adiponectin secretion enhancer comprising the material as an active ingredient thereof.

Also disclosed is a method for enhancing secretion of adiponectin from adipocytes. Further disclosed is a method for treating a disease related to insulin resistance.

BACKGROUND ART

Adiponectin is a type of protein secreted from adipocytes. Normal adipocytes secrete adiponectin and are sensitive to insulin. In obese patients adipocytes can accumulate adipose and become hypertrophied, which results in the decreased secretion of adiponectin. Decreased adiponectin secretion leads to the increased secretion of TNF-α and resistin, which can cause insulin resistance. This leads to diseases such as metabolic syndrome, diabetes, hypertension, hyperlipidemia, obesity, or arteriosclerosis. Therefore, increases in adiponectin secretion from adipocytes can prevent and ameliorate diseases, such as metabolic syndrome, diabetes, hypertension, hyperlipidemia, obesity or arteriosclerosis.

The mechanism of the adiponectin secretion from adipocytes has yet to be explained. Qiang, et al. (Molecular and Cellular Biology, 2007, 27 4698-4707) recites that activities of Ero1-Lα, an endoplasmic reticulum oxidoreductase, and modulators of peroxisome proliferator-activated receptor γ (PPARγ), and SIRT1, an NAD-dependent deacetylation enzyme, control the secretion of adiponectin in 3T3-L1 adipocytes. In addition, it has been reported that insulin tolerance disorders can be treated or prevented by increasing protein levels and activities of sirtuins, such as SIRT1 (published Japanese Translation No. 2007-527418 of PCT international Publication WO2005065667A3).

Nicotinamide mononucleotide (NMN) is an intermediate metabolite from synthesis of the coenzyme $NAD^+$. In recent years, NMN has been reported to have an ameliorative effect on secretory ability of insulin in aged mice, a dramatic enhancement of insulin sensitivity and secretion in high fat diet and aging induced type 2 diabetes in mice (U.S. Pat. No. 7,737,158), and a remarkable enhancement of mitochondrial function in aged muscle. Moreover, it is reported that administration of NMN is useful in improving and preventing the symptoms of various age-related diseases, such as obesity, increased serum lipid levels, decreased insulin sensitivity, memory decline, and deterioration of optical function, such as macular degeneration (WO 2014/146044).

SUMMARY

An object of the present disclosure is to provide a material that can be ingested safely and is capable of increasing the secretion of adiponectin. The present inventors have demonstrated that β-NMN enhances secretion of adiponectin.

The present teachings provide an adiponectin secretion enhancer, dietary supplement and feed. The present teachings also provide a method for enhancing secretion of adiponectin from adipocytes and a method for treating a disease related to insulin resistance as indicated below.

[1] An adiponectin secretion enhancer comprising β-NMN, a pharmaceutically acceptable salt thereof, or a solvate thereof.

[2] The secretion enhancer of [1] above, which is administered orally.

[3] A dietary supplement containing the secretion enhancer of [1] or [2] above that is ingested in order to increase the secretion of adiponectin.

[4] A feed containing the secretion enhancer of [1] or [2] above that is ingested in order to increase the secretion of adiponectin.

[5] A method of enhancing adiponectin secretion, comprising administrating an effective amount of β-NMN, a pharmaceutically acceptable salt thereof, or a solvate thereof as an active ingredient to an animal.

[6] The method according to [5], wherein the effective amount of β-NMN, a pharmaceutically acceptable salt thereof, or a solvate thereof increases adiponectin secretion ability of adipocytes by 20% or more.

[7] The method according to [5] or [6] wherein the β-NMN, a pharmaceutically acceptable salt thereof, or a solvate thereof is administered orally.

[8] A method for treating a disease related to insulin resistance comprising administering an effective amount of β-NMN, a pharmaceutically acceptable salt thereof, or a solvate thereof as an active ingredient to an animal affected with the disease to improve adiponectin secretion ability of adipocytes.

[9] The method according to [8], wherein the adiponectin secretion ability of adipocytes increases by 20% or more compared to before the administering.

[10] The method according to [8] or [9] wherein the β-NMN, a pharmaceutically acceptable salt thereof, or a solvate thereof is administered orally.

The adiponectin secretion enhancer of the present teachings comprises β-NMN, which is inherently present in the body, as an active ingredient thereof, and is able to enhance secretion of adiponectin from adipocytes and increase the secretion thereof. In some configurations, the secretion enhancer can further comprise a solvate. In various configurations, the secretion enhancer can further comprise a pharmaceutically acceptable excipient. β-NMN is inherently present in the body and enhances secretion of adiponectin from adipocytes and increases the secretion thereof. Consequently, the secretion enhancer according to the present teachings can be ingested safely without causing adverse side-effects and is effective for preventing and treating diseases including insulin-resistance related diseases caused by decreased secretion of adiponectin.

In various embodiments, a method for enhancing adiponectin secretion can enhance the secretion of adiponectin, thereby improving insulin sensitivity and secretion. In some configurations, the method for treating a disease related to insulin resistance can effectively treat and improve symptoms or conditions of an animal including a human affected with the disease without causing adverse side-effects by increasing the secretion of adiponectin from the adipocytes.

BRIEF DESCRIPTION OF THE DRAWINGS

FIG. 6, including FIGS. 6A-6J depicts graphs indicating various results obtained by administering β-NMN to ANKO mice in Example 5.

DETAILED DESCRIPTION

In various embodiments, a secretion enhancer of the present teachings may also be a pharmaceutically acceptable salt of β-NMN. In some configurations, the pharmaceutically acceptable salt may be a salt of an inorganic acid or salt of an organic acid having a basic site in the manner of an amine. In some configurations, an acid salt can comprise acetic acid, benzenesulfonic acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid and p-toluenesulfonic acid. In various configurations, the pharmaceutically acceptable salt of β-NMN can be an alkaline salt, or organic salt having an acidic site in the manner of carboxylic acid. In various configurations, a salt can include a base derived from an alkaline metal salt or an alkaline earth metal salt, such as sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N'-dibenzylethylenediamine, chloroprocaine, procaine, diethanolamine, N-benzylphenethylamine, diethylamine, piperazine, or tris(hydroxymethyl)aminomethane or tetramethylammonium hydroxide.

In some embodiments, a secretion enhancer of the present teachings can comprise free β-NMN, a pharmaceutically acceptable salt of β-NMN, or a solvate thereof.

In various embodiments, a secretion enhancer of the present teachings can further comprise at least one additional active ingredient. In various configurations, the at least one additional active ingredient can comprise adipocyte differentiation promoting substances, fat accumulation inhibitory substances, lipolysis promoting substances or fat metabolism improving substances. In various configurations, the additional active ingredient can comprise taurine, glutathione, carnitine, creatine, coenzyme Q, glucuronic acid, glucuronolactone, capsicum extract, ginger extract, cacao extract, guarana extract, garcinia extract, theanine, γ-aminobutyric acid, capsaicin, capsiate, various organic acids, flavonoids, polyphenols, catechins, xanthine derivatives, or indigestible oligosaccharides such as fructooligosaccharides and polyvinylpyrrolidone.

In various embodiments, the secretion enhancer can further comprise a nontoxic pharmaceutical carrier or excipient. In some configurations, the secretion enhancer can be administered as an oral dosage form or a parenteral dosage form. In some configurations, the oral dosage form can comprise a solid preparation or liquid preparation. In some configurations, the solid preparation can be a tablet, a granule, a powder, a capsule, or a soft capsule. In various configurations, a liquid preparation can be a solution, a suspension, an emulsion, or a freeze-dried preparation. In various configurations, a parenteral dosage form can be an injection preparation, a suppository, an inhalant, or a percutaneously absorbed preparation.

The secretion enhancer of the present teachings can be administered to an animal. In some configurations, the animal can be a mammal. In various configurations, the animal can be a human, livestock, an experimental animal, or a pet. In various configurations, the mammal can be a cow, a pig, a horse, a sheep, a goat, a donkey, a monkey, a dog, a cat, a rabbit, a mouse, a rat, or a guinea pig. In various configurations, the mammal can be a human.

In some embodiments, a daily adult dosage as the amount of β-NMN can be 0.1 mg to 10 g, 0.5 mg to 7 g, 10 mg to 5 g or 100 mg to 2 g. In some configurations, the daily dose can be administered in a single dose. In various configurations, the daily adult dosage can be divided among multiple administrations.

In various embodiments, a method of enhancing adiponectin secretion can comprise administrating an effective amount of β-NMN or a pharmaceutically acceptable salt thereof to an animal in need thereof. In some configurations, the animal can be a human.

In various embodiments, a method for treating a disease related to insulin resistance can comprise administrating an effective amount of a secretion enhancer to an animal in need thereof. In some configurations, the secretion enhancer can be a β-NMN. In various configurations, the animal can be a mammal. In various configurations, the mammal can be a human.

In various embodiments, a method of treating an insulin related disease can comprise the administration of the effective amount ofβ-NMNs to an animal in need thereof. In some configurations, an insulin resistance related disease can be metabolic syndrome, diabetes, hyperlipidemia, fatty liver disease, hypertension, obesity or arteriosclerosis. In some configurations the fatty liver disease can be alcoholic fatty liver disease and non-alcoholic fatty liver disease.

In various embodiments, a method of preventing insulin resistance can comprise administration of an effective amount of a secretion enhancer to healthy animals.

In various embodiments, an animal feed can comprise a secretion enhancer of the present teachings. In various configurations, the animal feed can be a powder, a granule, a particle, a tablet, a capsule, soft capsule or a paste. In some configurations, the animal feed can be eaten directly or mixed into the animal diet or drinking water.

In various embodiments, a dietary supplement can comprise a secretion enhancer of the present teachings. In various configurations, the dietary supplement can be a powder, a granule, a particle, a tablet, a capsule, soft capsule or a paste. In some configurations, the dietary supplement can be taken as a supplement. In various configurations, the dietary supplement can be mixed into an animal feed, a food, or a beverage. In various configurations, a powdered dietary supplement can be dissolved in a beverage. In various configurations, the beverage can be water, alcohol, fruit juice, milk, or a carbonated beverage.

In some embodiments, the adiponectin secretion enhancer of the present teachings ("the secretion enhancer" or "the enhancer") comprises NMN (chemical formula: $C_{11}H_{15}N_2O_8P$) and enhances secretion of adiponectin from adipocytes and increases the secretion thereof. Consequently, it is preferable as an active ingredient of an orally administered composition or externally applied composition for preventing or treating diseases caused by decreased secretion of adiponectin, such as but without limitation metabolic syndrome, diabetes, hyperlipidemia, fatty liver, hypertension, obesity or arteriosclerosis. In some embodiments, an adiponectin secretion enhancer of the present teachings can comprise β-NMN. β-NMN is inherently present in the body and enhances secretion of adiponectin from adipocytes and increases the secretion thereof. Consequently, the secretion enhancer according to the teachings can be ingested safely without causing adverse side-effects and is effective for preventing and treating diseases including insulin-resistance related diseases caused by decreased secretion of adiponectin.

Although NMN has two types of optical isomers consisting of α- and β-forms, the NMN serving as an active ingredient of the secretion enhancer of the present teachings is β-NMN (CAS NO. 1094-61-7). The structure of β-NMN is indicated below.

[Chemical Formula 1]

β-NMN

The β-NMN used as an active ingredient may be prepared by any method. For example, purified β-NMN that is artificially synthesized by a chemical synthesis method, an enzymatic method or a fermentation method can be used as an active ingredient. In addition, since β-NMN is a component that is present throughout the body, β-NMN prepared by extraction or purification from a natural raw material such as an animal, plant or microorganism can be used. In addition, commercially available purified β-NMN may also be used.

As an example of a method for synthesizing β-NMN, β-NMN can be produced by reacting nicotinamide and L-ribose tetraacetate followed by phosphorylating the resulting NMN. As an example of an enzymatic method, β-NMN can be produced from nicotinamide and 5'-phosphoribosyl-1'-pyrophosphate (PRPP) using nicotinamide phosphoribosyl transferase (NAMPT). As an example of a fermentation method, nicotinamide phosphoribosyl transferase (NAMPT) can be produced from nicotinamide using a microbial metabolic system expressing NAMPT.

The secretion enhancer of the present teachings may also be a pharmaceutically acceptable salt of β-NMN. The pharmaceutically acceptable salt may be a salt of an inorganic acid or salt of an organic acid having a basic site in the manner of an amine. Examples of acids comprising such acid salts include acetic acid, benzenesulfonic acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid and p-toluenesulfonic acid. In addition, the pharmaceutically acceptable salt of β-NMN may be an alkaline salt or organic salt having an acidic site in the manner of carboxylic acid. Examples of bases comprising such acid salts include alkaline metal salts and alkaline earth metal salts derived from bases such as sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N'-dibenzylethylenediamine, chloroprocaine, procaine, diethanolamine, N-benzylphenethylamine, diethylamine, piperazine, tris(hydroxymethyl) aminomethane or tetramethylammonium hydroxide.

The active ingredient of the secretion enhancer of the present teachings can comprise free β-NMN, a solvate or a pharmaceutically acceptable salt of β-NMN. Examples of solvents that form the solvate include water and ethanol.

A secretion enhancer of the present teachings may also contain another active ingredient in addition to β-NMN.

There are no particular limitations on the other active ingredients provided they do not impair the effect of β-NMN of increasing the adiponectin secretion. Examples of other ingredients include known adipocyte differentiation promoting substances, fat accumulation inhibitory substances, lipolysis promoting substances, and fat metabolism improving substances. Specific examples of these other ingredients include taurine, glutathione, carnitine, creatine, coenzyme Q, glucuronic acid, glucuronolactone, capsicum extract, ginger extract, cacao extract, guarana extract, garcinia extract, theanine, γ-aminobutyric acid, capsaicin, capsiate, various organic acids, flavonoids, polyphenols, catechins, xanthine derivatives, and indigestible oligosaccharides such as fructooligosaccharides and polyvinylpyrrolidone.

In some embodiments, a secretion enhancer of the present teachings can comprise only the active ingredient or may contain other components. For example, the enhancer can be formulated in various drug forms using routine pharmaceutical means by combining the active ingredient with a nontoxic pharmaceutical carrier or excipient. Examples of drug forms of the enhancer used in oral dosage forms include solid preparations such as tablets, granules, powders, capsules or soft capsules, liquid preparations such as solutions, suspensions or emulsions, and freeze-dried preparations. Examples of parenteral dosage forms include injection preparations as well as suppositories, inhalants and percutaneously absorbed preparations.

Examples of nontoxic pharmaceutical carriers used in formulation include sugars such as glucose, lactose, sucrose, fructose or reduced maltose, carbohydrates such as starch, hydroxyethyl starch, dextrin, β-cyclodextrin, crystalline cellulose or hydroxypropyl cellulose, sugar-alcohols such as mannitol, erythritol, sorbitol or xylitol, esters such as fatty acid glycerides or polyoxyethylene sorbitan fatty acid esters, polyethylene glycol, ethylene glycol, amino acids, albumin, casein, silicon dioxide, water and physiological saline. In addition, commonly used additives, such as stabilizers, lubricants, humectants, emulsifiers, suspending agents, binders, disintegration agents, solvents, solubilizing agents, buffers, isotonic agents, antiseptics, correctives or colorants. The carriers can be suitably added as necessary for formulation of the enhancer.

The secretion enhancer of the present teachings can be administered to a human or another animal. Non-limiting examples of other animals include mammals such as cows, pigs, horses, sheep, goats, donkeys, monkeys, dogs, cats, rabbits, mice, rats or guinea pigs. The enhancer can be administered to or ingested by a human, livestock, experimental animal or pet, and is preferably administered to or ingested by a human.

The dosage or ingested amount of the secretion enhancer of the present teachings can be suitably selected or determined according to species, age (such as monthly age), body weight, symptoms or severity of disease of a human or animal to be administered the enhancer as well as the administration schedule or type of the formulation. For example, the daily adult dosage as the amount of β-NMN can be 0.1 mg to 10 g, 0.5 mg to 7 g, 10 mg to 5 g or 100 mg to 2 g. The daily dose can be administered in a single dose or divided among multiple administrations.

β-NMN is considered to have a high degree of safety since it is a biological component that is also contained in foods. Therefore, the secretion enhancer of the present teachings can also be used as an active ingredient of a dietary supplement ingested in order to increase the secretion of adiponectin. Dietary supplements are soft foods that provide nutritional support for the purpose of maintaining or improving health, and include foods for specified health uses, functional nutritional foods and health foods. Since the secretion enhancer of the teachings is highly safe and is suitable for long-term continuous ingestion, a dietary supplement containing the enhancer is expected to demonstrate superior therapeutic and ameliorative action against diseases related to the insulin resistance such as metabolic syndrome, diabetes, hyperlipidemia, fatty liver (alcoholic fatty liver and non-alcoholic fatty liver), hypertension, obesity or arteriosclerosis.

The secretion enhancer of the present teachings can also be used in an animal feed in order to increase the secretion of adiponectin. Administration of this feed to livestock, pets or experimental animals and the like increases the amount of adiponectin secreted from adipocytes of the animal ingesting the enhancer, and as a result of subsequently enhancing insulin sensitivity in the animal, can be expected to demonstrate prevention or amelioration of diseases such as metabolic syndrome, diabetes, hypertension, hyperlipidemia, fatty liver (alcoholic fatty liver and non-alcoholic fatty liver), obesity or arteriosclerosis.

The method for enhancing adiponectin secretion comprises administrating an effective amount of β-NMN, a pharmaceutically acceptable salt thereof, or a solvate thereof (to also be referred to as "β-NMNs") or the aforementioned secretion enhancer of the invention to animals including humans. The method can enhance the secretion of adiponectin and thereby improve insulin sensitivity and secretion. This method can increase the adiponectin secretion ability of adipocytes by 20% or more, preferably 50% or more, more preferably 70% or more, further more preferably 80% or more, most preferably 100% or more than prior to the administration.

In various embodiments, a method for treating a disease related to insulin resistance can comprise administrating an effective amount of β-NMNs, or the aforementioned secretion enhancer of the present teachings to animals including humans affected with the insulin resistance. The method can effectively treat and improve symptoms or conditions of the animals affected with the disease by increasing the secretion of adiponectin from the adipocytes without causing adverse side-effects. Furthermore, the method can increase the adiponectin secretion ability of adipocytes by 20% or more, preferably 50% or more, more preferably 70% or more, further more preferably 80% or more, most preferably 100% or more than before the administration.

These methods of the present teachings can be expected to treat or improve the symptoms or conditions of the animals including humans affected with the insulin resistance related disease by improving the adiponectin secretion ability of adipocytes thereof.

The methods can improve the adiponectin secretion ability of adipocytes by the administration of the effective amount of β-NMNs as an active ingredient, or the aforementioned secretion enhancer of the present teachings to an animal affected with the insulin resistance, thereby treating or improving the insulin resistance related disease. The insulin resistance related diseases include metabolic syndrome, diabetes, hyperlipidemia, fatty liver (alcoholic fatty liver and non-alcoholic fatty liver), hypertension, obesity or arteriosclerosis. Furthermore, the methods of the present teachings can prevent animals without insulin resistance from developing these diseases by the administration of the effective amount β-NMNs as an active ingredient, or the aforementioned secretion enhancer.

The dietary supplement or feed according to the present teachings can be produced by forming an edible form such as a powder, granule, particle, tablet, capsule, soft capsule or paste using commonly used means following addition of a suitable excipient or the like to β-NMN. The dietary supplement of the present teachings may be ingested as is, or may be ingested after having been mixed with various foods and beverages. For example, a powdered dietary supplement can be ingested in a state in which it has been dissolved or dispersed in a beverage such as water, alcohol, fruit juice, milk or carbonated beverage. The feed of the present teachings may also be made to be ingested by an animal directly or may be made to be ingested in a state in which it has been mixed with other solid feed or drinking water.

The dietary supplement and feed of the present teachings can contain other food materials or various additives. Examples of food materials include vitamins, sugars, proteins, lipids, dietary fiber and fruit juices. Specific examples include members of the vitamin B group such as vitamin B1 derivatives, vitamin B2, vitamin B6, vitamin B12, vitamin B13, biotin, pantothenic acid, nicotinic acid or folic acid, tat-soluble vitamins such as vitamin E, vitamin D or derivatives thereof, vitamin K1, vitamin K2 or β-carotene, minerals such as calcium, potassium, iron or zinc, yeast, L-carnitine, creatine, α-lipoic acid, glutathione, glucuronic acid, taurine, collagen, soy isoflavones, lecithin, peptides, amino acids, γ-aminobutyric acid, diacylglycerol, DHA, EPA, capsaicin, chondroitin sulfate, agaric mushroom extract, carrot extract, garlic extract, vegetable juice, lecithin, royal jelly, propolis, octacosanol, tlavangenol, pycnogenol, mica, chitosan, garcinia extract, chondroitin and glucosamine. Examples of additives include sweeteners, sour agents such as organic acids, stabilizers, fragrances and colorants.

EXAMPLES

Although the following provides a more detailed explanation of the present invention by indicating examples thereof, the invention is not limited to the following examples.

Mice and Rats

The CD(SD) rats, C57BL/6N mice and C57BL/6J mice used in the following experiments were kept in an SPF environment throughout the entire experimental period.

Oral Administration

A solution prepared by dissolving β-NMN (Oriental Yeast Co., Ltd.) in water for injection (Otsuka Pharmaceutical Co., Ltd.) or PBS (phosphate-buffered saline) was orally administered by gavage using a metal gastric tube (Fuchigami Kikai Co., Ltd.) attached to a polypropylene disposable syringe (Terumo Corp.).

Intraperitoneal Administration

A solution prepared by dissolving β-NMN (Oriental Yeast Co., Ltd.) in PBS (phosphate-buffered saline) was administered intraperitoneally in accordance with the method of Dr. Sinclair (Gomes, et al., Cell, 2013, Vol. 155, p. 1624-1638) and the method of Dr. Imai (Yoshino, et al., Cell Metabolism, 2011, Vol. 14, p. 528-536).

Measurement of Adiponectin Levels

Measurement of adiponectin levels in the following experiments was carried out in the manner indicated below.

Antibody Preparation

Anti-mouse adiponectin polyclonal antibody (Oriental Yeast Co., Ltd.) was adjusted to 10 μg/mL with PBS for use as primary antibody solution. In addition, anti-mouse adiponectin polyclonal antibody (Oriental Yeast Co., Ltd.) was biotinylated and adjusted to 2 μg/mL for use as secondary antibody solution.

Standard Preparation

Mouse adiponectin (Oriental Yeast Co., Ltd.) was adjusted to 45.2 ng/mL with specimen diluent for use as standard.

Standard Solution/Sample Preparation

The 45.2 ng/mL standard was serially diluted two-fold with specimen diluent to prepare 22.6 ng/mL, 11.3 ng/mL, 5.65 ng/mL, 2.83 ng/mL, 1.41 ng/mL, 0.71 ng/mL and 0.35 ng/mL standard solutions. Furthermore, the specimen diluent was used for the 0 ng/mL standard solution. In addition, the specimens were prepared by serially diluting two-fold with the specimen diluent to a dilution factor of 808-fold in the case of rat serum or 6161-fold in the case of mouse serum.

ELISA

First, 100 μl of primary antibody solution was added to each well of a 96-well plate. The plate covered with sealing film was incubated overnight at 4° C. 350 μl of washing solution (PBS containing 0.05% Tureen 20) was added to each well, and the washing solution was immediately removed. This washing procedure was carried out three times. 300 of blocking solution was added to each well, and the plate covered with sealing film was incubated overnight at 4° C. The aforementioned washing procedure was carried out three times.

100 μl of the standard solutions and specimen were added to respectively designated wells, and the plate covered with sealing film was incubated for 1 hour at 25° C. The reaction solution was removed and the aforementioned washing procedure was carried out three times. 100 μL t of the secondary antibody solution was added to each well, and the plate covered with sealing film was incubated for 1 hour at 25° C. The reaction solution was removed and the aforementioned washing procedure was carried out three times. Subsequently, 100 μL of a 2000-fold serial dilution of enzyme-labeled streptavidin (Dako Corp., # P0397) was added to each well, and the plate covered with sealing film was incubated for 1 hour at 25° C. The reaction solution was removed and the aforementioned washing procedure was carried out three times.

Moreover, 100 μl of substrate solution (Becton Dickinson & Co., TMB Substrate Reagent Set, #555214) were added to each well, and the plate covered with sealing film was incubated for 15 minutes at 25° C. After stopping the reaction by adding 100 μL of 2 N sulfuric acid to each well, the absorbance of each well was measured at a primary wavelength of 450 nm and a secondary wavelength of 570 nm with a plate reader (FLOUstar Optima, BMG LabTech Ltd.). Furthermore, since the mouse adiponectin polyclonal antibody used in ELISA cross-reacts with rat adiponectin, levels of rat adiponectin were measured as mouse adiponectin by using standard mouse adiponectin.

Example 1

PBS with or without β-NMN was orally administered to CD rats (4 weeks old, males and females) for 28 days.

The doses of β-NMN are shown in Table 1. Males (n=6) were used in groups 1, 2 and 3, while females (n=6) were used in groups 4, 5 and 6.

TABLE 1

| Group | β-NMN Dose |
|---|---|
| 1 | 0 mg/kg/day |
| 2 | 250 mg/kg/day |
| 3 | 1000 mg/kg/day |

TABLE 1-continued

| Group | β-NMN Dose |
|---|---|
| 4 | 0 mg/kg/day |
| 5 | 250 mg/kg/day |
| 6 | 1000 mg/kg/day |

Figure 1:
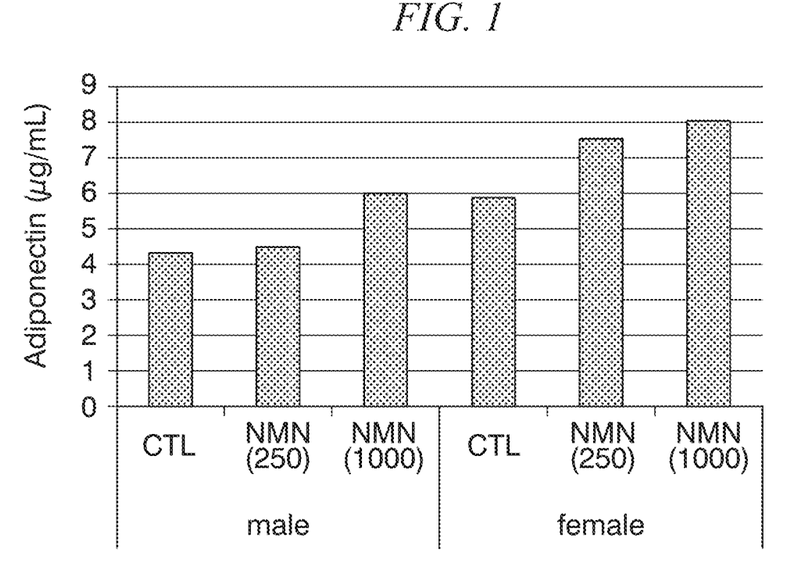
FIG. 1 is a graph indicating the results of measuring adiponectin levels in the serum of rats in groups orally administered β-NMN in Example 1.

Rat serum adiponectin levels were measured on day 28 from the start of administration. The results are shown in FIG. 1. In the graph, "CTL", "NMN(250)" and "NMN (1000)" refer to β-NMN doses of 0 mg/kg/day, 250 mg/kg/day and 1000 mg/kg/day, respectively. β-NMN increased serum adiponectin levels dose-dependently regardless of the gender of the rats. These results showed that administration of β-NMN increased the secreted amounts of adiponectin.

Example 2

PBS with or without β-NMN was orally administered to C57BL/6N mice (8 months old, females) for 4 days. The doses of β-NMN in three groups (n=4) are shown in Table 2.

TABLE 2

| Group | β-NMN Dose |
|---|---|
| 1 | 0 mg/kg/day |
| 2 | 125 mg/kg/day |
| 3 | 625 mg/kg/day |

Figure 2:
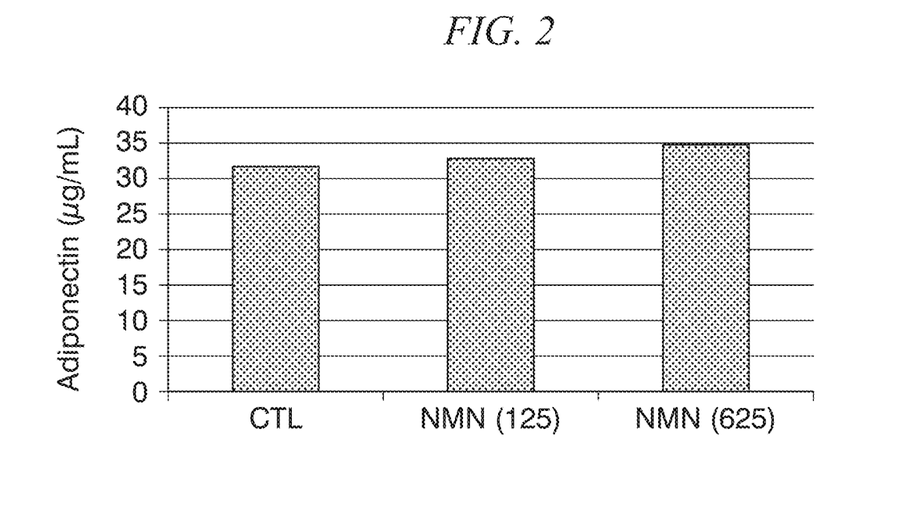
FIG. 2 is a graph indicating the results of measuring adiponectin levels in the serum of rats in groups orally administered β-NMN in Example 2.

Mouse serum adiponectin levels were measured on day 4 from the start of administration. The results of the measurement are shown in FIG. 2. In the graph, "CTL", "NMN (125)" and "NMN(625)" refer to β-NMN doses of 0 mg/kg/day, 125 mg/kg/day and 625 mg/kg/day, respectively. When the results for groups 1, 2 and 3 were compared, β-NMN increased serum adiponectin levels dose-dependently. These results showed that administration of β-NMN increased the secreted amounts of adiponectin.

Example 3

PBS with or without β-NMN was administered intraperitoneally to C57BL/6J mice (8 months old, females) for 4 days. The doses of β-NMN in each group (n=3) are shown in Table 3.

TABLE 3

| Group | β-NMN Dose |
|---|---|
| 1 | 0 mg/kg/day |
| 2 | 625 mg/kg/day |
| 3 | 1250 mg/kg/day |

Figure 3:
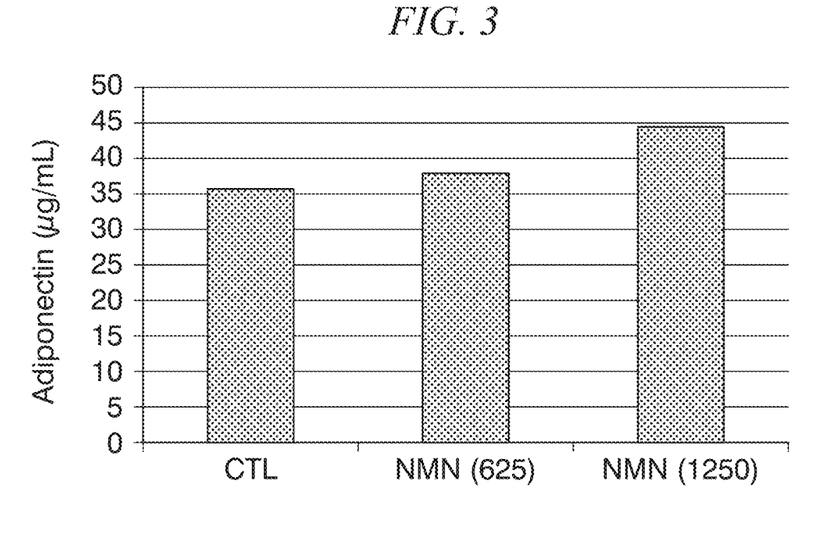
FIG. 3 is a graph indicating the results of measuring adiponectin levels in the serum of mice in groups intraperitoneally administered β-NMN in Example 3.

Mouse serum adiponectin levels were measured on day 4 from the start of administration. The results are shown in FIG. 3. In the graph, "CTL", "NMN(625)" and "NMN (1250)" refer to β-NMN doses of 0 mg/kg/day, 625 mg/kg/day and 1250 mg/kg/day, respectively. When the results for groups 1, 2 and 3 were compared, β-NMN increased serum adiponectin levels dose-dependently.

Example 4

3T3-L1 cells were differentiated into adipocytes and then the cells were stimulated with β-NMN to measure the secreted amount of adiponectin.

The 3T3-L1 cells were differentiated into adipocytes in the manner described below.

First, 3T3-L1 cells were seeded in a 24-well plate at $5 \times 10^4$ cells/well followed by culturing for 2 to 3 days in culture medium (DMEM containing 10% fetal bovine serum (FBS)) at 37° C. in 5% $CO_2$. Next, the culture medium was replaced with a first differentiation-inducing medium (containing 10 μM dexamethasone, 5 μM 3-isobutyl-1-methylxanthine (IBMX) and 10 μg/mL of insulin) followed by culturing for 2 days at 37° C. in 5% $CO_2$. The medium was replaced with the second differentiation-inducing medium (containing 10 μg/mL of insulin) followed by culturing for 2 days at 37° C. in 5% $CO_2$. Subsequently, the medium was twice replaced with culture medium every 2 to 3 days to differentiate the 3T3-L1 cells into mature adipocytes.

Figure 4:
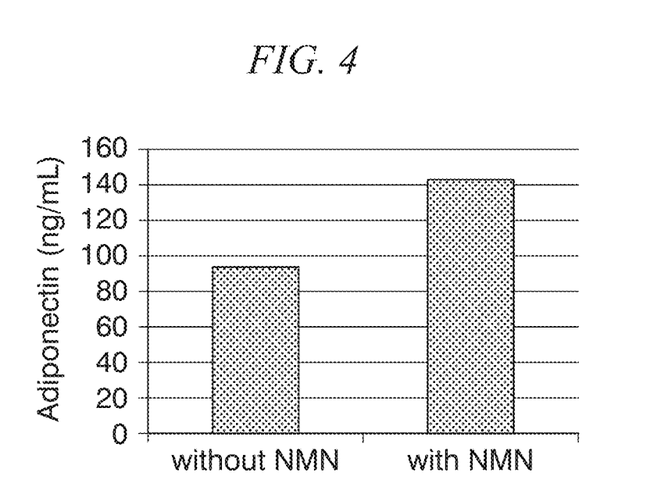
FIG. 4 is a graph indicating the results of measuring the amounts of adiponectin secreted from adipocytes differentiated from mouse fibroblast 3T3-L1 cells stimulated with β-NMN in Example 4.

3T3-L1 adipocytes were cultured in the presence ("NMN addition") or absence ("NMN non-addition") of β-NMN for 7 days. The amount of adiponectin secreted into the culture supernatant was measured. The results of measurement of adiponectin levels in the culture supernatant are shown in. FIG. 4. As a result, adiponectin levels were higher in adipocytes cultured with β-NMN than in adipocytes cultured without β-NMN, and secretion of adiponectin was enhanced by stimulation with β-NMN.

Example 5

The present inventors investigated mice adipocyte-specifically deficient in NAMPT (adipose tissue-specific NAMPT knockout mice, to be referred to as "ANKO mice"), which is the rate-limiting enzyme in $NAD^+$ biosynthesis and is known to decrease in the adipose tissue of obese and aged rodents and humans. As a result, the ANKO mice exhibited severe insulin resistance in adipose tissue, liver and skeletal muscle (data not shown), and demonstrated adipose tissue dysfunction represented by an increase in plasma free fatty acid concentrations and decrease in the plasma concentration of adiponectin, which is the major insulin-sensitive adipokine (data not shown). Moreover, the ANKO mice also exhibited increased phosphorylation of cyclin-dependent kinase 5 (CKD5) and peroxisome proliferator-activated receptor-gamma (PPARγ) (serine at amino acid position 273), and expression of the target gene of phosphorylated PPARγ associated with obesity in adipose tissue was decreased (data not shown).

Figure 5:
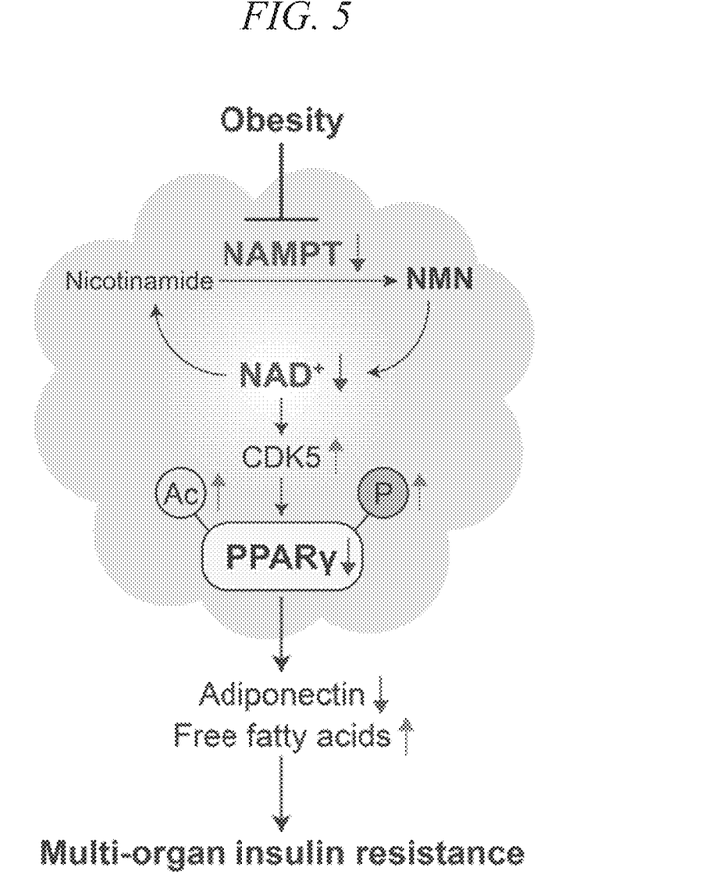
FIG. 5 is a schematic diagram indicating the relationship between an NAMPT-mediated metabolic pathway and acquisition of insulin resistance.

FIG. 5 is a schematic diagram indicating the relationship between the NAMPT-mediated metabolic pathway and acquisition of insulin resistance.

When expression levels of NAMPT decrease due to obesity, production of NMN from nicotinamide decreases and $NAD^+$ levels decrease. Due to this decrease in NAD levels, CDK5 activity increases and phosphorylation of PPARγ increases. As a result, the amount of adiponectin secreted from adipocytes decreases and the amount of free fatty acid increases, thereby resulting in insulin resistance in multiple organs.

Figure 6A:
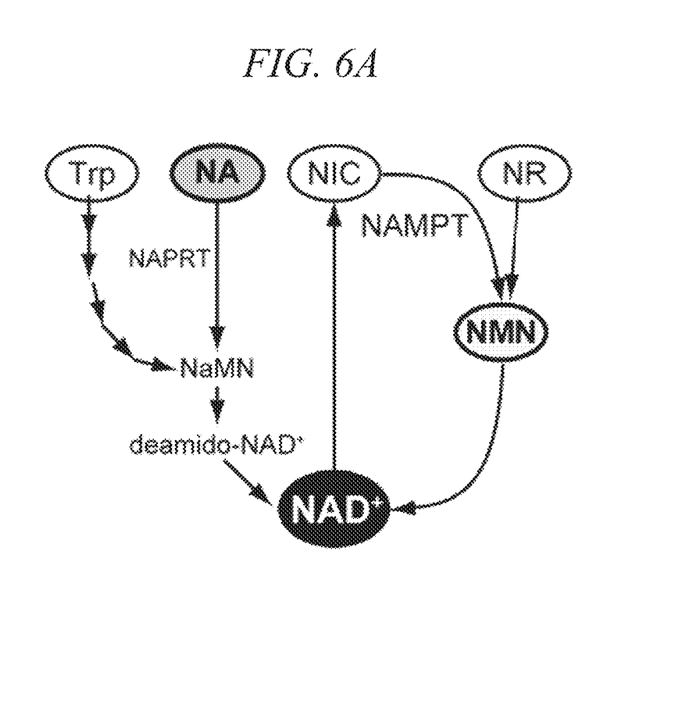
FIG. 6A indicates a schematic diagram of the NAD$^+$ biosynthesis pathway in humans.

To determine whether metabolic derangements depend on the defects in NAD+ biosynthesis in ANKO mice, we treated mice with NMN, a key NAD+ intermediate and the product of the NAMPT reaction (FIG. 6A). In the diagram, "NA" represents nicotinic acid, "NaMN" represents nicotinic acid mononucleotide, "NIC" represents nicotinamide, "NR" represents nicotinamide riboside, "Tip" represents tryptophan, and "NAPRT" represents nicotinate phosphoribosyl transferase. NMN is a product of an enzyme reaction mediated by NAMPT and is converted directly to NAD+. Nicotinic acid is a precursor in the NAPRT-dependent NAD+ biosynthesis pathway.

ANKO mice were generated by using adiponectin-Cre transgenic mice and floxed-Nampt mice as previously described (Noon et al., 2015). Mice were maintained on a standard chow diet (LabDiet 5053; LabDiet) ad libitum. For RSG rescue experiments, ANKO mice received a chow containing RSG (#71740; Cayman Chemical) at the approximate dose of 20 mg/kg body Weight/day soon after weaning for up to 7 weeks. For NAD+ precursor rescue experiments, we administered NMN (#44500900; Oriental Yeast) and NA (#72309; Sigma-Aldrich) in drinking water, at the approximate dose of 500 mg/kg of body weight, to ANKO mice soon after weaning for up to 2 months.

More specifically, drinking water containing NMN (500 mg/kg body weight/day) was administered to the female ANKO mice and metabolic parameters were investigated after administering NMN for 4 to 6 weeks. The results are shown in FIGS. 6B to 6J. In the graphs, "NMN-ANKO" indicates the results for NMN-treated ANKO mice, "ANKO" indicates the results for NMN-untreated ANKO mice of the same age as the NMN-treated ANKO mice, and "flox/flox" indicates the results for the control mice (female Nampt-floxed (flox/flox) mice). All values in the graphs represent the mean ±SE. In the graphs, "*" indicates p<0.05, "" indicates p<0.01, and "*" indicates p<0.001 (NMN-treated ANKO mice vs. NMN-untreated ANKO mice, Student's t-test). In addition, in the graphs, "a" indicates p<0.05 (NMN-treated ANKO mice vs. NMN-untreated ANKO mice, ANOVA), and "b" indicates p<0.05 (control mice vs. NMN-untreated ANKO mice, ANOVA).

Figure 6B:
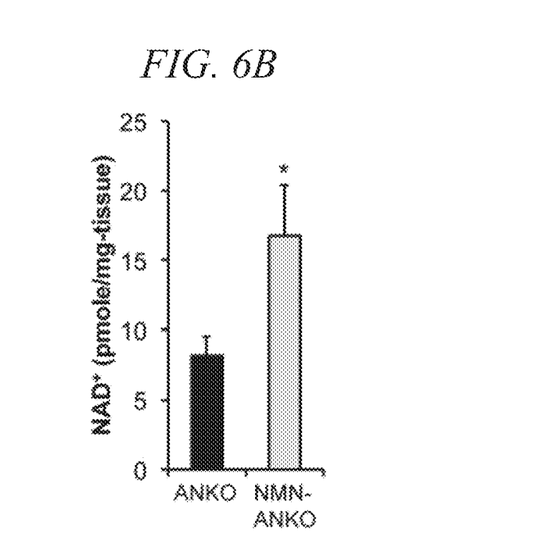
FIG. 6B indicates the results of measuring NAD$^-$ levels in adipose tissue for female ANKO mice administered NMN for 4 to 6 weeks (500 mg/kg body weight/day) and non-dosed female ANKO mice of the same age (per group, n=5 to 7) in Example 5.
Figure 6C:
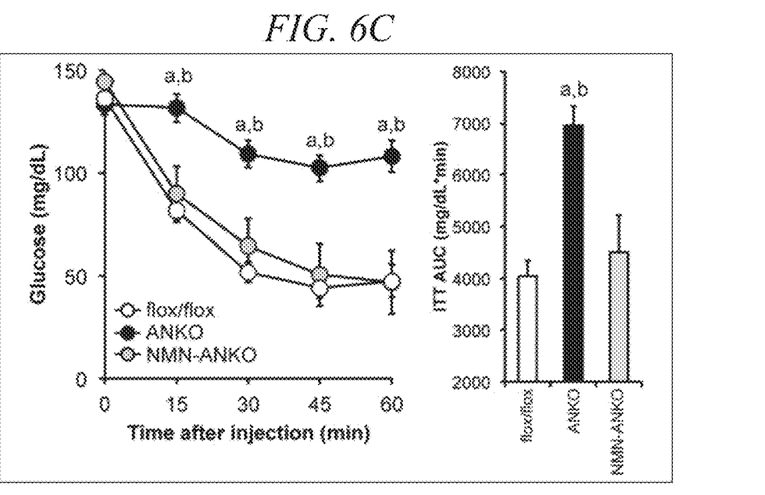
FIG. 6C indicates the results of having carried out an insulin tolerance test (ITT) in Example 5. The left graph in FIG. 6C indicates the results for changes in glucose concentration over time (insulin tolerance curve), while the graph on the right side of FIG. 6C indicates the results for the area under the curve (AUC) of glucose concentration.

FIG. 6B indicates the results of measuring NAD⁻ levels in adipose tissue for female ANKO mice administered NMN for 4 to 6 weeks (500 mg/kg body weight day) and non-dosed female ANKO mice of the same age (per group, n=5 to 7). NAD+ levels were measured with an HPLC (high-performance liquid chromatography) system using a Supelco LC-18-T column (#58970-U, Sigma-Aldrich Corp.) (Yoon, et al., Cell Metabolism, 2015, Vol. 21, p. 706-717). FIG. 6C indicates the results of having carried out an insulin tolerance test (ITT), consisting of administering insulin and measuring blood glucose concentration over time, on NMN-treated mice following administration of NMN for 4 weeks (n=7) and non-dosed ANKO mice for which age has been aligned at 2 to 3 weeks (n=14), and control mice (n=8). The left graph in FIG. 6C indicates the results for changes in glucose concentration over time (insulin tolerance curve), while the graph on the right side of FIG. 6C indicates the results for the area under the curve (AUC) of glucose concentration.

Figure 6D:
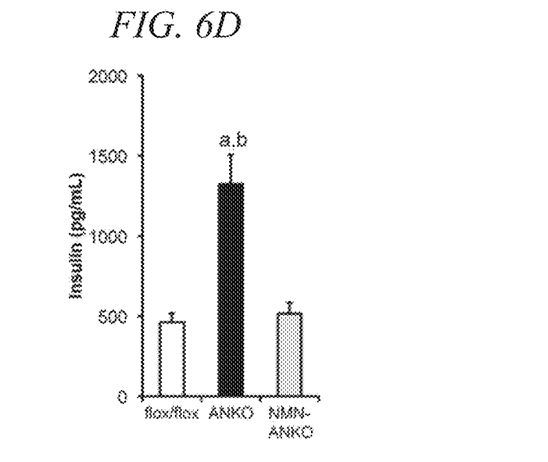
FIG. 6D shows the results for measuring plasma insulin concentrations for NMN-treated ANKO mice, NMN-untreated ANKO mice and control mice in Example 5.
Figure 6E:
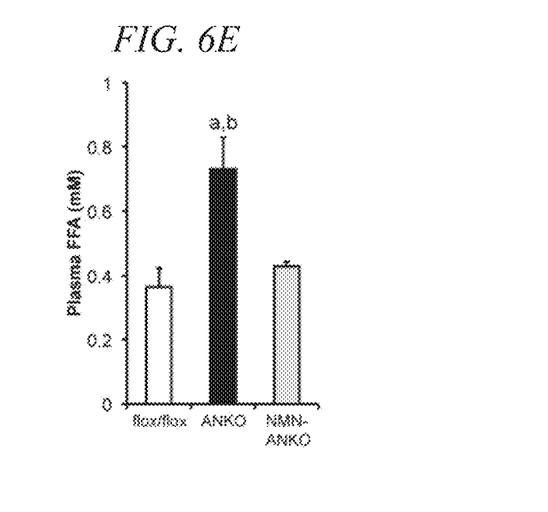
FIG. 6E shows the results of measuring plasma free fatty acid (FFA) concentrations for NMN-treated ANKO mice, NMN-untreated ANKO mice and control mice in Example 5.

The results for measuring plasma insulin concentrations for NMN-treated ANKO mice, NMN-untreated ANKO mice and control mice are shown in FIG. 6D, while the results of measuring plasma free fatty acid (FFA) concentrations are shown in FIG. 6E (per group, n=5 to 11). In addition, visceral adipose tissue was respectively sampled from NMN-treated ANKO mice and NMN-untreated ANKO mice followed by measurement of the levels of PPARγ (Ser273), CDK5 and nuclear protein acetylated lysine in the visceral adipose tissue (per group, n=3 to 4). The results of determining the phosphorylation rate of PPARγ (Ser273) in each group ([phosphorylated PPARγ(Ser273)]/[PPARγ(Ser273)] are shown in FIG. 6F, the results of determining the phosphorylation rate of CDK5 ([phosphorylated CDK5]/[CDK5]) are shown in FIG. 6G, and the results of determining the acetylation rate of nuclear protein lysine ([acetylated lysine]/[Lamin B1]) are shown in FIG. 6H.

Moreover, expression levels of each gene targeted by obesity-associated. PPARγ (Ser273) were investigated for visceral adipose tissue respectively sampled from NMN-treated ANKO mice and NMN-untreated. ANKO mice. The results are shown in FIG. 6I (per group, n=4 to 5). In addition, FIG. 6J indicates the results of measuring plasma adiponectin concentrations and plasma adipsin concentrations in NMN-treated ANKO mice and NMN-untreated ANKO mice (per group, n=5 to 12).

NMN administration significantly increased adipose tissue NAD+ concentrations in ANKO mice (FIG. 6B). NMN administration improved insulin sensitivity in ANKO mice compared to the age-matched untreated ANKO mice (FIG. 6C). The insulin responses in NMN-treated ANKO mice were similar to those in the age-matched control mice, suggesting that NMN administration normalized the insulin resistance phenotype. NMN administration also normalized plasma insulin and FFA concentrations in ANKO mice (FIG. 6D and FIG. 6E). However, NMN did not change body weight (ANKO=18.1±0.4; NMN-treated ANKO=18.0±0.5 g), daily food intake (ANKO=0.22±0.01; NMN-treated ANKO=0.21±0.01 g/g of body weight), or body temperature (ANKO=36.7±0.2; NMN-treated ANKO=36.7±0.3_C) during this relatively short period of treatment.

Figure 6F:
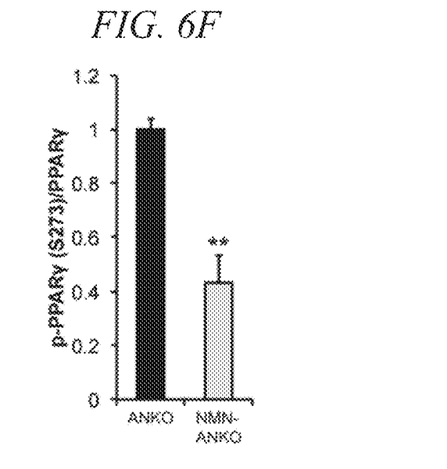
FIG. 6F shows the results of determining the phosphorylation rate of PPARγ (Ser273) in each group ([phosphorylated PPARγ(Ser273)]/[PPARγ(Ser273)] in Example 5.
Figure 6G:
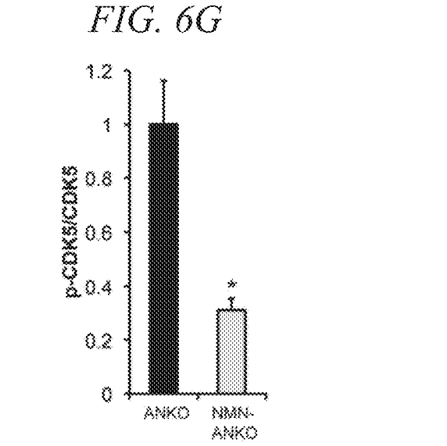
FIG. 6G shows the results of determining the phosphorylation rate of CDK5 ([phosphorylated CDK5]/[CDK5]) in Example 5.
Figure 6H:
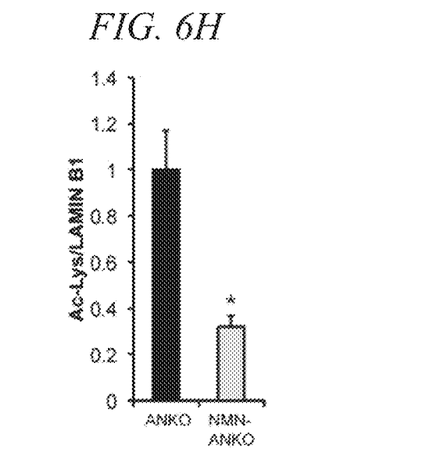
FIG. 6H shows the results of determining the acetylation rate of nuclear protein lysine ([acetylated lysine]/[Lamin B1]) in Example 5.
Figure 6I:
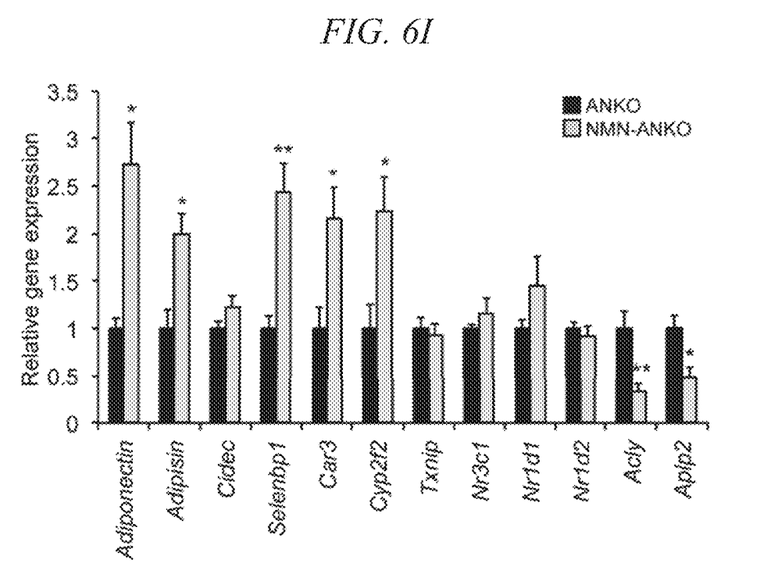
FIG. 6I shows the results of expression levels of each gene targeted by obesity-associated. PPARγ (Ser273) in visceral adipose tissue respectively sampled from NMN-treated ANKO mice and NMN-untreated ANKO mice.
Figure 6J:
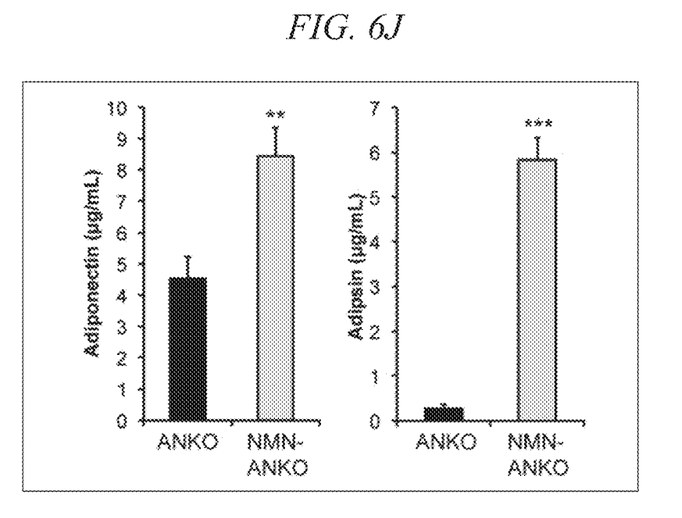
FIG. 6J indicates the results of measuring plasma adiponectin concentrations and plasma adipsia concentrations in NMN-treated. ANKO mice and NMN-untreated ANKO mice.

NMN administration decreased phosphorylation of PPARγ (Ser273) and CDK5 in VAT (FIG. 6F and FIG. 6G). In addition, NMN-treated ANKO mice reduced global nuclear lysine acetylation (FIG. 6H), indicating that NMN administration could increase activity of nuclear NAD+-dependent protein deacetylases such as SIRT1. Adipose tissue gene expression and plasma concentrations of adiponectin and adipsin were restored by NMN administration (FIG. 6I and FIG. 6J). In addition, we confirmed that adipose tissue expressed nicotinic acid phosphoribosyltransferase (NAPRT) (data not shown) and tested the effect of 5- to 7-week administration of nicotinic acid (NA) (500 mg/kg body weight/day), the precursor in the NAPRT-dependent NAD+ biosynthetic pathway (FIG. 6A).

Since metabolic disorders of ANKO mice were improved by administration of β-NMN or nicotinic acid, the NAD⁺ biosynthesis pathway mediated by NAMPT in adipose tissue was indicated to be important for controlling metabolic function in adipose tissue and throughout the body, and systemic metabolic disorders associated with obesity, and particularly multi-organ insulin resistance, were indicated to be able to be treated and prevented as a result of promoting secretion of adiponectin by administering β-NMN.

What is claimed is:

1. A method for enhancing adiponectin secretion, comprising administering to a subject with a disease related to insulin resistance caused by decreased secretion of adiponectin a pharmaceutically effective amount of β-nicotinamide mononucleotide, a pharmaceutically acceptable salt thereof or a solvate thereof, wherein the disease related to insulin resistance is selected from the group consisting of metabolic syndrome, a fatty liver disease, hypertension, and arteriosclerosis.

2. The method in accordance with claim 1, wherein the pharmaceutically effective amount of β-nicotinamide mononucleotide, a pharmaceutically acceptable salt thereof, or a solvate thereof increases adiponectin secretion of adipocytes by 20% or more.

3. The method in accordance with claim 1, wherein the administering a pharmaceutically effective amount of β-nicotinamide mononucleotide, a pharmaceutically acceptable salt thereof, or a solvate thereof is orally administering a pharmaceutically effective amount of β-nicotinamide mononucleotide, a pharmaceutically acceptable salt thereof, or a solvate thereof.

4. The method in accordance with claim 3, wherein the oral administration comprises adding the β-nicotinamide mononucleotide, a pharmaceutically acceptable salt thereof, or a solvate thereof to the subject's food or drink.

5. The method in accordance with claim 3, comprising adding to the subject's drink a powder comprising the pharmaceutically effective amount of β-nicotinamide mononucleotide, a pharmaceutically acceptable salt thereof, or a solvate thereof.

6. The method in accordance with claim 1, wherein the subject is a mammal.

7. The method in accordance with claim 6, wherein the mammal is a human.

8. A method in accordance with claim 1, wherein the fatty liver disease is selected from the group consisting of alcoholic fatty liver disease and non-alcoholic fatty liver disease.

9. A method in accordance with claim 1, wherein the pharmaceutically effective amount of β-nicotinamide mononucleotide, a pharmaceutically acceptable salt thereof or a solvate thereof is in a formulation further comprising at least one additional active ingredient.

10. A method in accordance with claim 9, wherein the at least one additional active ingredient is selected from the group consisting of an adipocyte differentiation promoting substance, a fat accumulation inhibitory substance, a lipolysis promoting substance, and a fat metabolism improving substance.

11. A method in accordance with claim 1, wherein the method further comprises administering a substance selected from the group consisting of taurine, glutathione, carnitine, creatine, coenzyme Q, glucuronic acid, glucuronolactone, capsicum extract, ginger extract, cacao extract, guarana extract, garcinia extract, theanine, γ-aminobutyric acid, capsaicin, capsiate, various organic acids, flavonoids, polyphenols, catechins, xanthine derivatives, and indigestible oligosaccharides.

12. A method in accordance with claim 1, wherein the administering comprises administering 0.1 mg to 10 g of β-NMN per day.

* * * * *